(12) United States Patent
Asleson et al.

(10) Patent No.: US 11,291,471 B2
(45) Date of Patent: Apr. 5, 2022

(54) INTERVENTIONAL MEDICAL SYSTEMS FOR DELIVERY OF A MEDICAL ELECTRICAL LEAD TO AN EPICARDIAL IMPLANT SITE

(71) Applicant: Medtronic, Inc., Minneapolis, MN (US)

(72) Inventors: Andrea J. Asleson, Maple Grove, MN (US); Teresa A. Whitman, Dayton, MN (US); Kelly M. Wien, Big Lake, MN (US)

(73) Assignee: Medtronic, Inc., Minneapolis, MN (US)

( * ) Notice: Subject to any disclaimer, the term of this patent is extended or adjusted under 35 U.S.C. 154(b) by 311 days.

(21) Appl. No.: 16/538,649

(22) Filed: Aug. 12, 2019

(65) Prior Publication Data

US 2019/0357939 A1 Nov. 28, 2019

Related U.S. Application Data

(62) Division of application No. 14/878,010, filed on Oct. 8, 2015, now Pat. No. 10,433,870.

(51) Int. Cl.
*A61B 17/34* (2006.01)
*A61M 25/01* (2006.01)
(Continued)

(52) U.S. Cl.
CPC .... *A61B 17/3468* (2013.01); *A61B 17/00234* (2013.01); *A61B 17/3415* (2013.01);
(Continued)

(58) Field of Classification Search
CPC ............ A61B 17/3468; A61B 17/3415; A61B 17/00234; A61B 2017/00243;
(Continued)

(56) References Cited

U.S. PATENT DOCUMENTS 3,952,742 A 4/1976 Taylor
5,454,787 A 10/1995 Lundquist
(Continued)

FOREIGN PATENT DOCUMENTS

CN 1976730 A 6/2007
CN 103108597 A 5/2013
(Continued)

OTHER PUBLICATIONS

German patent application entitled "Apparatus for Transcutaneous Implantation of Epicardial Heart Pacemaker Electrodes", pp. 1-28.
(Continued)

*Primary Examiner* — Diane D Yabut
(74) *Attorney, Agent, or Firm* — Shumaker & Sieffert, P.A.

(57) ABSTRACT

A medical system comprising a guiding catheter having an inflation lumen. The inflation lumen extends within a handle and a shaft of the guiding catheter. An inflatable sleeve has a proximal end and a distal end, with the ends attached to the guiding catheter. A sealed interior portion of the inflatable sleeve is bounded by the inflatable sleeve and the shaft of the guiding catheter, and in fluid communication with a distal port of the inflation lumen. The system further comprises a delivery catheter defining a delivery lumen and configured for sliding engagement within the guide lumen of the guiding catheter.

20 Claims, 7 Drawing Sheets

(51) Int. Cl.
*A61N 1/05* (2006.01)
*A61N 1/372* (2006.01)
*A61B 17/00* (2006.01)
*A61B 17/22* (2006.01)

(52) U.S. Cl.
CPC ......... *A61N 1/0587* (2013.01); *A61N 1/0592* (2013.01); *A61N 1/372* (2013.01); *A61B 2017/00243* (2013.01); *A61B 2017/00323* (2013.01); *A61B 2017/00336* (2013.01); *A61B 2017/22069* (2013.01); *A61M 25/0147* (2013.01); *A61M 25/0152* (2013.01)

(58) Field of Classification Search
CPC .... A61B 2017/22069; A61M 25/0147; A61M 25/0152; A61N 1/372; A61N 1/0592
See application file for complete search history.

(56) References Cited

U.S. PATENT DOCUMENTS

| | | | |
|---|---|---|---|
| 5,634,895 A | | 6/1997 | Igo et al. |
| 5,702,417 A | | 12/1997 | Hermann |
| 5,833,650 A | * | 11/1998 | Imran ............... A61M 25/1011 604/509 |
| 6,836,687 B2 | | 12/2004 | Kelley et al. |
| 6,979,290 B2 | | 12/2005 | Mourlas et al. |
| 7,162,309 B2 | | 1/2007 | Laske et al. |
| 7,186,214 B2 | | 3/2007 | Ness |
| 7,691,047 B2 | | 4/2010 | Ferrari |
| 7,840,261 B2 | | 11/2010 | Rosenman et al. |
| 8,012,143 B1 | | 9/2011 | Kampa et al. |
| 8,287,532 B2 | | 10/2012 | Carroll et al. |
| 8,864,676 B2 | | 10/2014 | Beasley et al. |
| 9,119,738 B2 | | 9/2015 | Fish |
| 9,486,281 B2 | | 11/2016 | Fung et al. |
| 10,433,870 B2 | | 10/2019 | Asleson et al. |
| 2001/0044591 A1 | | 11/2001 | Stevens et al. |
| 2004/0059348 A1 | | 3/2004 | Geske et al. |
| 2006/0173441 A1 | | 8/2006 | Gelfand et al. |
| 2010/0125281 A1 | | 5/2010 | Jacobson et al. |
| 2010/0312256 A1 | | 12/2010 | Kassab et al. |
| 2011/0130744 A1 | | 6/2011 | Kassab et al. |
| 2014/0121670 A1 | | 5/2014 | Bishop et al. |
| 2015/0065872 A1 | | 3/2015 | Drake et al. |
| 2015/0230699 A1 | | 8/2015 | Berul et al. |

FOREIGN PATENT DOCUMENTS

| | | |
|---|---|---|
| CN | 103153384 A | 6/2013 |
| WO | 2015078971 A2 | 6/2015 |

OTHER PUBLICATIONS

International Search Report of PCT/EP2014/075821, dated Jun. 18, 2015, 12 pages.
(PCT/US2016/054449) PCT Notification of the International Search Report and the Written Opinion of the International Searching Authority, dated Dec. 19, 2016, 16 pages.
Prosecution History from U.S. Appl. No. 14/878,010, dated Oct. 8, 2015 through Aug. 12, 2019, 64 pp.
First Office Action and Search Report, and translation thereof, from counterpart Chinese Application No. 201680058751.6, dated Sep. 17, 2020, 8 pp.

* cited by examiner

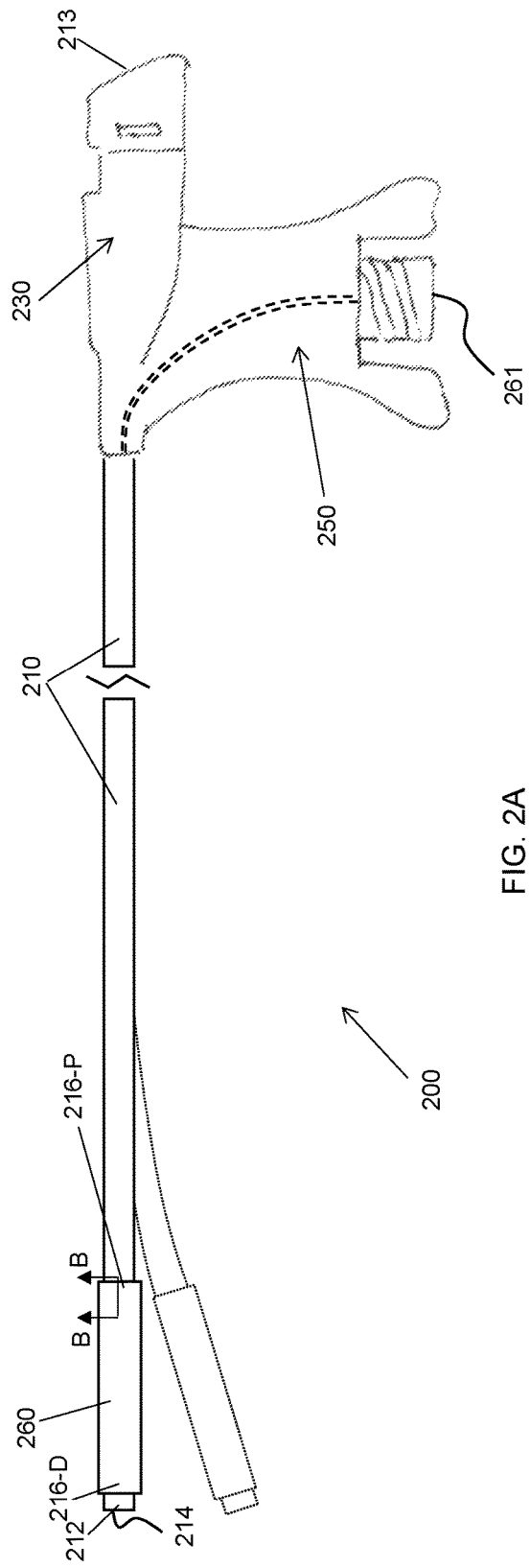
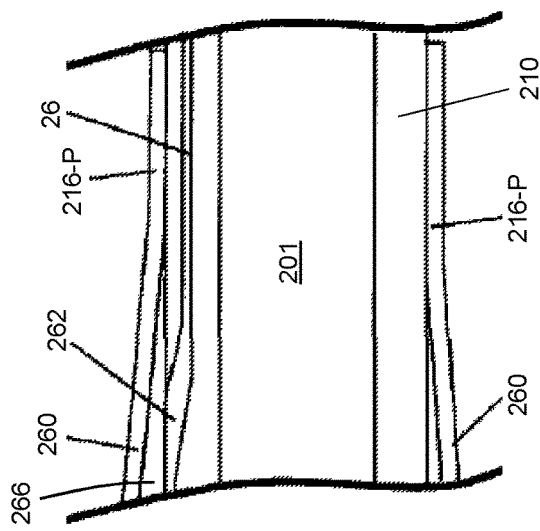
FIG. 2A
FIG. 2B ical lead on an epicardial surface 6 of the patient's
INTERVENTIONAL MEDICAL SYSTEMS FOR DELIVERY OF A MEDICAL ELECTRICAL LEAD TO AN EPICARDIAL IMPLANT SITE

RELATED APPLICATIONS

This application is a divisional of application Ser. No. 14/878,010, entitled "INTERVENTIONAL MEDICAL SYSTEMS AND METHODS FOR DELIVERING A MEDICAL ELECTRICAL LEAD TO AN EPICARCIAL IMPLANT SITE," filed Oct. 8, 2015, now U.S. Pat. No. 10,433,870, the contents of which are incorporated by reference in their entirety.

TECHNICAL FIELD

The present disclosure pertains to interventional medical systems, and more particularly to improved systems and associated methods for securing medical electrical leads to epicardial implant sites.

BACKGROUND

Implantable medical electrical leads, included in systems that are known in the art for delivering cardiac therapy and/or for providing cardiac monitoring, are often implanted transvenously within a heart of a patient. But extravascular implant sites may be preferred, for example, in those patients where vascular access is difficult, or because transvenous leads can become fibrosed in the heart over time, which makes lead revision and extraction procedures challenging.

FIG. 1 is a schematic showing an access site A for creating a passageway between a patient's diaphragm 19 and xiphoid process 20 of sternum 13, for example, to implant a medical electrical lead on an epicardial surface 6 of the patient's heart, which is enclosed within the pericardial sac 15. After making a superficial incision, an operator may open a passageway between diaphragmatic attachments 18 and diaphragm 19 by using blunt dissection tools and techniques that are known in the art. Then, the operator may employ a piercing tool to pass a guide wire through the pericardial sac 15, also according to methods known in the art. The operator may use fluoroscopic guidance to position a distal portion of the guide wire along a portion of epicardial surface 6, at which a target implant site is located, and then pass a guiding catheter over the positioned guide wire. The guiding catheter then serves as a conduit for delivery of an implantable medical electrical lead to the target implant site, but some difficulty may be encountered by the operator in securing the delivered lead to the implant site.

SUMMARY

Examples and methods for delivering an implantable medical electrical lead to a target implant site on an epicardial surface of a patient's heart, as disclosed herein, employ an inflatable sleeve of a guiding catheter together with a delivery catheter to alleviate difficulties in securing the delivered lead to the implant site.

According to some methods, after an operator positions the inflatable sleeve of the guiding catheter in proximity to the target implant site, the operator, by inflating the positioned sleeve, displaces the epicardial surface away from the overlying pericardial sac so that a gap between the displaced epicardial surface and a distal-most opening of a lumen of the guiding catheter is at least equal to a reach of a delivery catheter, which the operator advances through the lumen of the guiding catheter until a distal tip segment of the delivery catheter extends out through the distal-most opening thereof. With the epicardial surface displaced, and the distal tip segment of the delivery catheter extending out from the guide lumen, the operator can adjust an adjustable segment of the delivery catheter from a straight configuration to a curved configuration to activate the reach thereof within the gap created by the displacement of the epicardial surface, and then advance the lead through, and out a distal-most opening of a delivery lumen of the delivery catheter. The reach of the delivery catheter is defined as a maximum orthogonal distance from a proximal segment of the delivery catheter to a distal-most edge of the distal tip segment of the delivery catheter, wherein the adjustable segment extends from the proximal segment to the distal tip segment, and the distal-most edge of the distal tip segment defines the distal-most opening of the delivery lumen; and the reach of the delivery catheter may orient a fixation member of the lead relative to the epicardial surface in a way that enables the operator to secure the lead to the surface with the fixation member. According to some examples, the inflatable sleeve of the guiding catheter is a non-compliant sleeve that has a maximum diameter of at least twice the reach of the delivery catheter, when inflated, and a distal-facing surface of the inflated sleeve is located no more than 0.25 inch (6.4 mm) from the distal-most opening of the guide lumen, being proximal thereto.

The details of one or more examples are set forth in the accompanying drawings and the description below. Other features, objects, and advantages will be apparent from the description and drawings, and from the claims.

BRIEF DESCRIPTION OF DRAWINGS

FIG. 2A is a plan view of a guiding catheter employed by an interventional medical system, according to some examples.

FIG. 2B is a cross section view through section line B-B of FIG. 2A, according to some examples.

DETAILED DESCRIPTION

Figure 1:
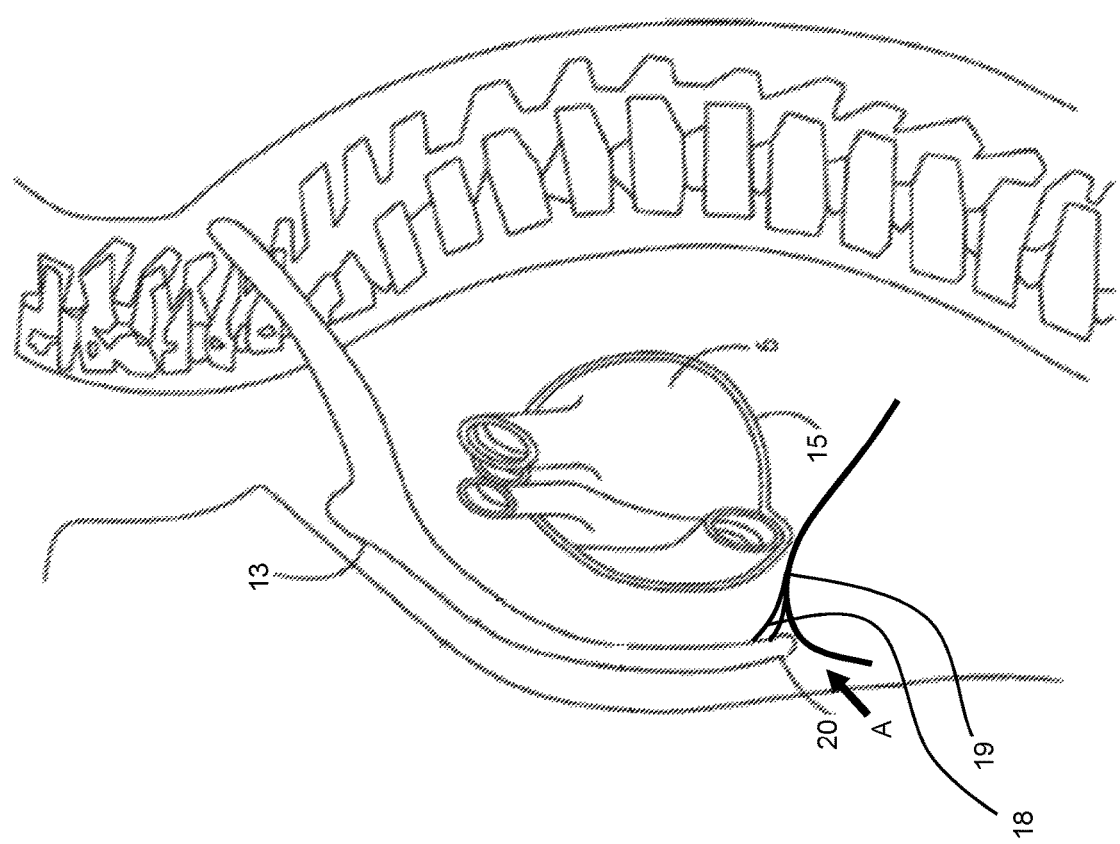
FIG. 1 is a schematic depicting a sub-sternal access site through which a medical electrical lead may be implanted on an epicardial surface of a patient's heart.

The following detailed description is exemplary in nature and is not intended to limit the scope, applicability, or configuration of the disclosure in any way. Rather, the following description provides practical examples, and those skilled in the art will recognize that some of the examples may have suitable alternatives.

FIG. 2A is a plan view of a guiding catheter 200 employed by an interventional medical system, according to some examples; and FIG. 2B is a cross-section view through section line B-B of FIG. 2A, according to some examples. FIGS. 2A-B illustrate guiding catheter 200 including a shaft 210, a hub 230, a handle 250, and an inflation assembly, wherein shaft 210 defines a guide lumen 201, hub 230 defines a proximal opening 213 into guide lumen 201, handle 250 is joined to hub 230 and to a proximal end of shaft 210, and the inflation assembly includes an inflatable sleeve 260 and an inflation lumen 26. According to the illustrated example, inflation lumen 26 extends from a proximal port 261 thereof, within handle 250 (dashed lines), to a distal port 262 thereof formed in shaft 210 (FIG. 2B), and inflatable sleeve 260, which is preferably formed from a non-compliant polymer material, such as polyethylene terephthalate (PET), has proximal and distal ends 216-P, 216-D secured to shaft 210 so that a sealed interior portion 266 portion thereof is in fluid communication with inflation lumen 26 via distal port 262. According to some examples, and with reference to FIG. 4, when sleeve 260 is inflated, a distal-facing surface 264 thereof is located no more than 0.25 inch (6.4 mm) from a distal-most opening 214 of guide lumen 201. Sleeve 260 may be inflated, for example, by attaching an inflation syringe 560 to a luer fitting of proximal port 261, as shown in FIG. 5A.

In an example, shaft 210, which may be approximately 30 cm in length, is formed from a stainless steel braid reinforced polyether block amide of graduated stiffness (e.g., various grades of PEBAX® ranging in durometer from 40 D, along a distal length of shaft 210, to 72D, along a proximal length of shaft 210), wherein proximal end 216-P of sleeve 260 may be secured to a stiffer section of shaft 210 than distal end 216-D of sleeve 260 in some examples. Guide lumen 201 may have a diameter of between approximately 0.090 inch and approximately 0.100 inch. A distal end 212 of shaft 210, which defines distal-most opening 214 of guide lumen 201, is preferably formed from a relatively soft material to be atraumatic, for example, a polyurethane, such as Pellethane®, having a durometer of 80 A, wherein, according to some examples, a radiopaque filler, such as Tungsten, is blended therewith to provide fluoroscopic visualization thereof. Ends 216-P, 216-D of sleeve 260 may be secured to shaft 210 according to any suitable bonding method (thermal or adhesive) known to those skilled in the art. With further reference to FIG. 2A, shaft 210 may include a pre-formed curvature (dotted line) in proximity to, and proximal to inflatable sleeve 260, wherein no radius of the curvature is less than approximately 5 cm.

In the above-described example, inflation lumen 26 may be formed from an elongate polyimide tube, and handle 250 and hub 230 are molded from PEBAX® 7033, wherein a suitable method for assembling shaft 210 together with inflation lumen 26, handle 250, and hub 230 is described in paragraphs [0079]-[0082] of the commonly assigned United States Patent Application 2015/0065872, which paragraphs are hereby incorporated by reference. The '872 reference further describes a suitable sealing member that may be integrated into hub 230 to form proximal opening 213, according to some examples.

Figure 3A:
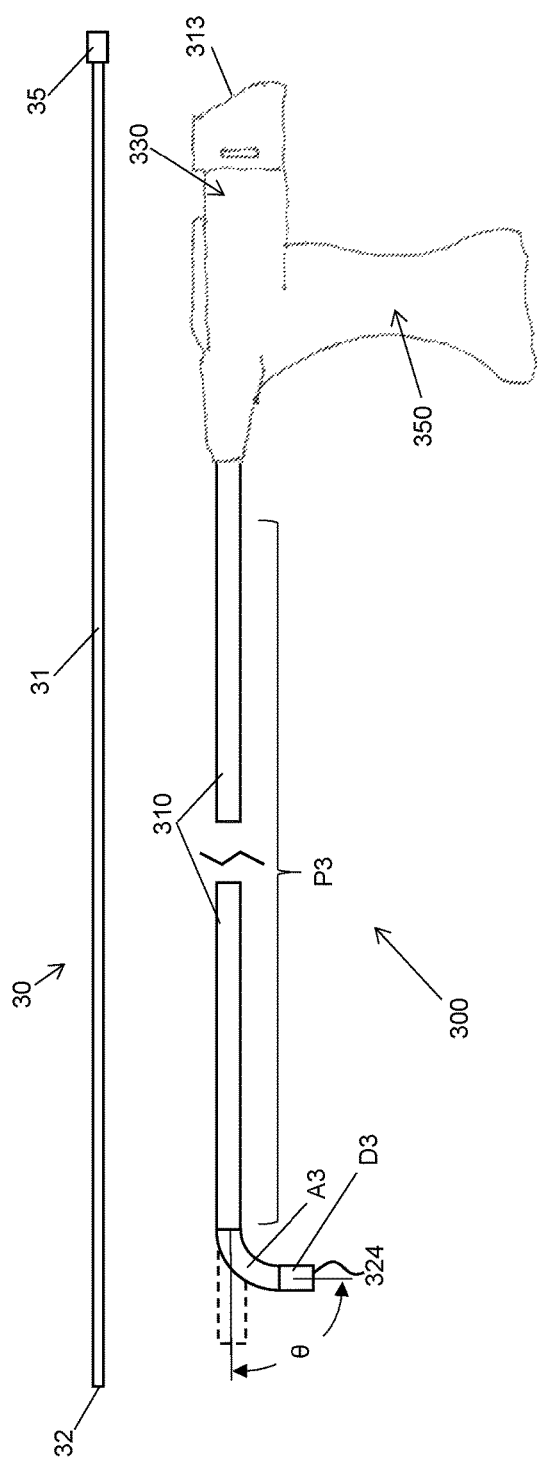
FIG. 3A is a plan view of a delivery catheter and a corresponding straightening member that may be employed in an interventional medical system with the guiding catheter of FIG. 2, according to some examples.

FIG. 3A is a plan view of a delivery catheter 300 and a corresponding straightening member 30 that may be employed in an interventional medical system with guiding catheter 200, according to some examples. FIG. 3A illustrates delivery catheter 300 including an elongate tubular member 310, a handle 350, and a hub 330, wherein tubular member 310 defines a delivery lumen 301 (FIG. 4) and is configured for sliding engagement within guide lumen 201 of guiding catheter 200, handle 350 is attached to hub 330 and to a proximal end of tubular member 310, and hub 330 defines a proximal opening 313 into delivery lumen 301. Hub 330 and handle 350 may be constructed and assembled together with tubular member 310 by the same methods disclosed in the aforementioned '872 reference for a catheter designated with reference numeral 100. Straightening member 30 is shown including a shaft 31 and a hub 35, which is attached to a proximal end of shaft 31, wherein shaft 31 is sized for sliding engagement within delivery lumen 301. Delivery lumen 301, which is also sized to receive passage of an implantable medical electrical lead therethrough, as described below, may have a diameter of between approximately 0.070 inch and approximately 0.080 inch.

FIG. 3A further illustrates tubular member 310 including a proximal segment P3, an adjustable segment A3, and a distal tip segment D3, wherein adjustable segment A3 extends from proximal segment P3 to distal tip segment D3 and is formed by a flexible sidewall. According to the illustrated example, the flexible sidewall of adjustable segment A3 is pre-formed to a curved configuration, which is adjustable to a straight configuration (dashed lines) by inserting straightening member shaft 31 through delivery lumen 301, until a distal tip 32 thereof extends within distal tip segment D3, so that tubular member 310 may be readily advanced through guide lumen 201 of guiding catheter 200. Once an operator has advanced distal tip segment D3 of tubular member 310 out through distal-most opening 214 of guide lumen 201, the operator may withdraw straightening member 30 from delivery lumen 301 of delivery catheter 300 to adjust adjustable segment A3 back to the curved configuration and thereby activate a reach R of delivery catheter tubular member 310, which is described in greater detail below, in conjunction with FIGS. 4 and 5B-C. With further reference to FIG. 3A, an angle θ through which distal tip segment D3 moves, between the straight configuration and the curved configuration of adjustable segment A3, is preferably no less than 45 degrees and no greater than 90 degrees, according to some examples.

According to some examples, tubular member proximal segment P3 is formed from a grade of PEBAX® having a durometer of approximately 72 D, adjustable segment A3 from a grade of PEBAX® having a durometer of approximately 25 D, and distal tip segment D3 from a relatively soft polyurethane like the aforementioned Pellethane® 80A. A length of proximal segment P3 may be approximately 12 inches (30 cm), a length of adjustable segment approximately 0.5 inch, and a length of distal tip segment D3 approximately 0.5 inch. Furthermore, straightening member shaft 31 may be formed from a relatively rigid medical grade plastic, such as high density polyethylene (HDPE).

Figure 3B:
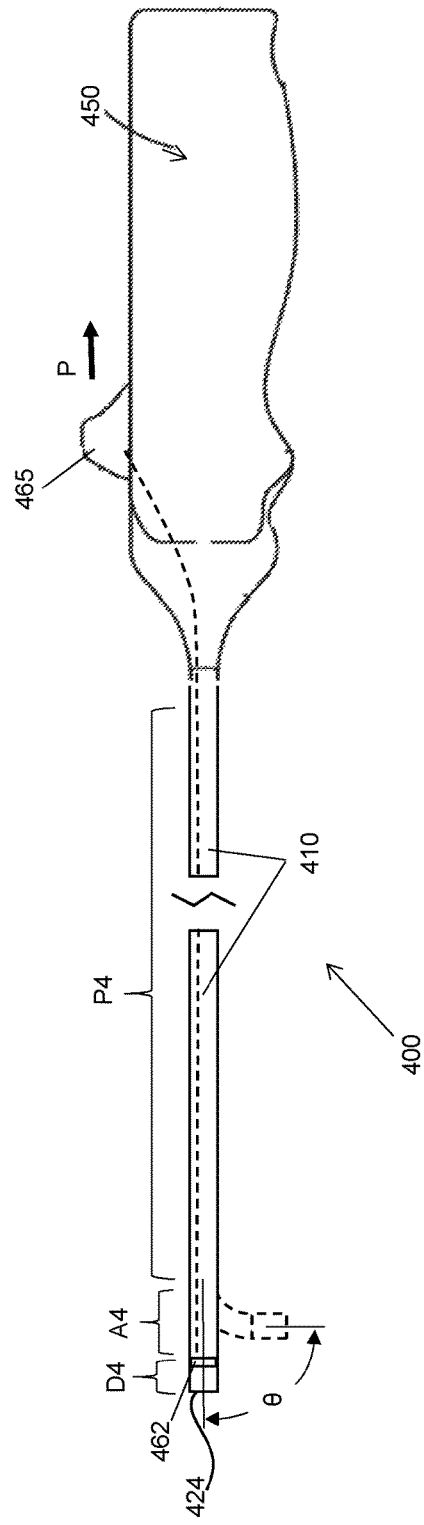
FIG. 3B is a plan view of a delivery catheter, according to some examples, which may be employed in lieu of the delivery catheter and straightening member of FIG. 3A.

FIG. 3B is a plan view of a delivery catheter 400, according to some examples, which may be employed in lieu of delivery catheter 300 and straightening member 30. FIG. 3B illustrates delivery catheter 400 including a tubular member 410 and a handle 450 into which a pull wire mechanism is integrated, wherein the pull wire mechanism is configured to adjust an adjustable segment A4 of tubular member 410 from a straight configuration to a curved configuration (dashed lines). Tubular member 410, like tubular member 310, defines a delivery lumen 401 (FIG. 4) sized to receive passage therethrough of an implantable medical electrical lead, and includes a proximal segment P4, a distal tip segment D4, and adjustable segment A4 extending therebetween, wherein suitable exemplary lengths and materials for each segment P4, A4, D4 are similar to those of each corresponding segment P3, A3, D3 of tubular member 310.

FIG. 3B further illustrates the pull wire mechanism of delivery catheter 400 including a pull band 462, an actuator 465, and a pull wire (dotted line), wherein pull band 462 is mounted to tubular member 410, in proximity to a transition from adjustable segment A4 to distal tip segment D4, actuator 465 is mounted to handle 450, and the pull wire extends therebetween, with a distal end thereof coupled to pull band 462 and a proximal end thereof coupled to actuator 465, so that moving actuator, per arrow P, causes the pull wire to adjust adjustable segment A4 from the straight to the curved configuration. Suitable constructions for the pull wire mechanism are known to those skilled in the art. It should be noted that angle θ through which distal tip segment D4 of tubular member 410 moves, between the straight configuration and the curved configuration of adjustable segment A4, is similar to that described above for distal tip segment D3 of tubular member 310.

Figure 4:
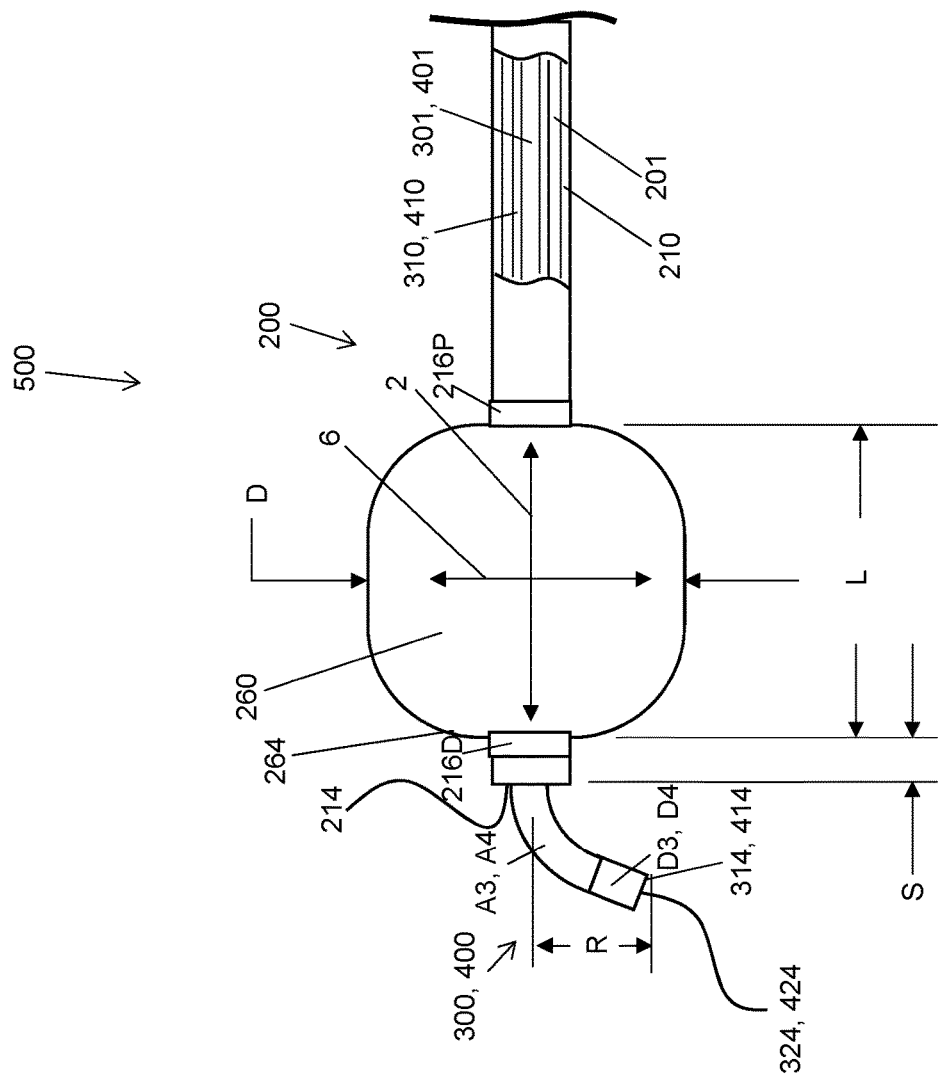
FIG. 4 is a plan view, with a partial cross-section view, of a distal portion of an interventional medical system, according to some examples.
Figure 5A:
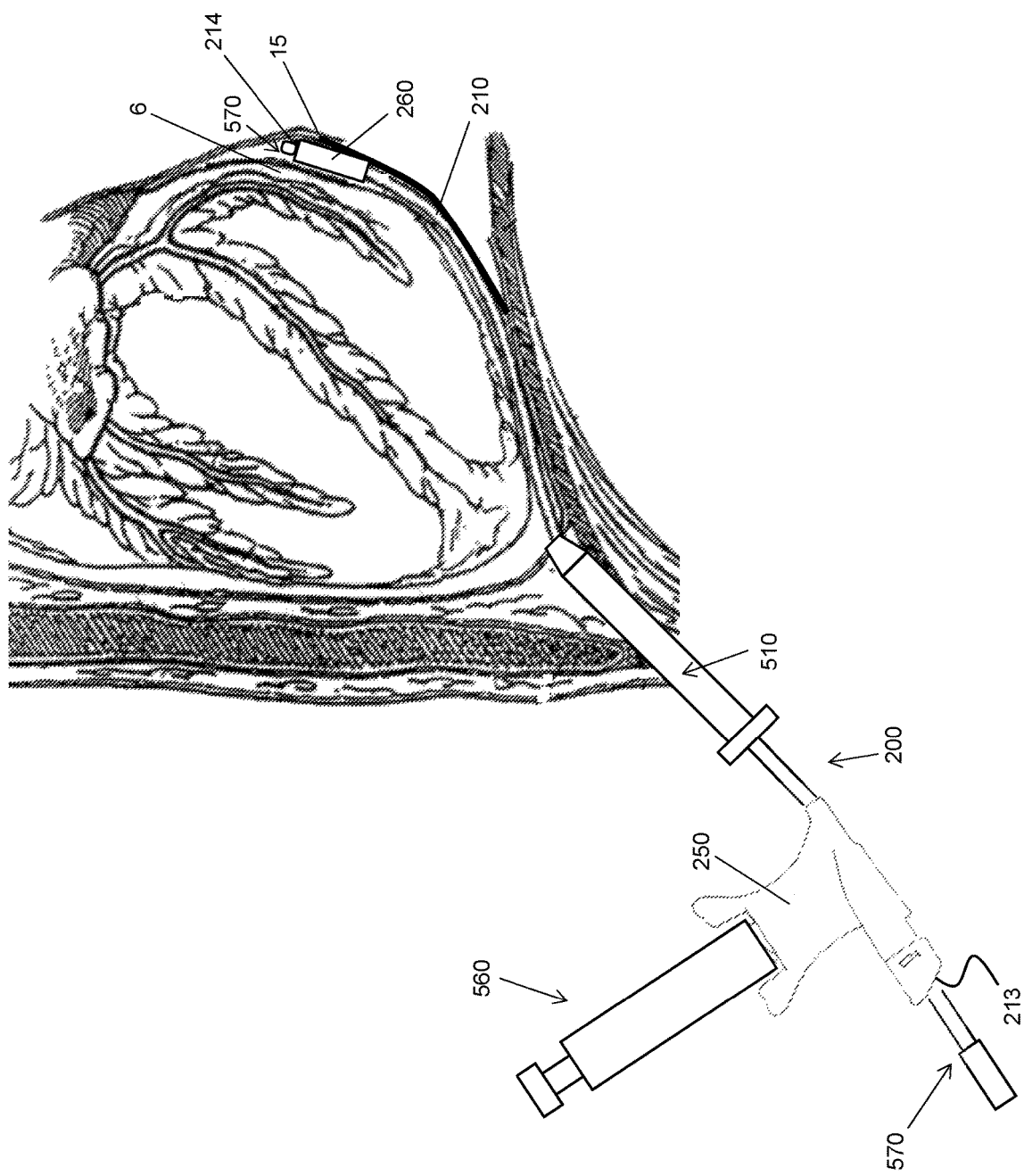
FIG. 5A is an example schematic of the disclosed medical system.

FIG. 4 is a plan view, with a partial cross-section view, of a distal portion of an interventional medical system 500, according to some examples, wherein inflatable sleeve 260 of guiding catheter 200 is inflated to a maximum diameter D thereof, and delivery catheter tubular member 310, 410 extends out from distal-most opening 214 of guiding catheter 200, with adjustable segment A3, A4 thereof adjusted to the curved configuration. FIG. 4 illustrates the aforementioned reach R of delivery catheter tubular member 310, 410 being defined as a maximum orthogonal distance from proximal segment P3, P4 to a distal-most edge 312, 412 of distal tip segment D3, D4, wherein distal-most edge 312, 412 defines a distal-most opening 324, 424 of delivery lumen 301, 401. Reach R may be between approximately 1 cm and approximately 2 cm, and, according to the illustrated example, maximum diameter D of the inflated sleeve 260 is at least twice reach R of delivery catheter tubular member 310, 410. According to some examples, maximum diameter D is between approximately 1.75 cm and approximately 3.5 cm, and a length L of the inflated sleeve 260 is between approximately 1.75 cm and approximately 3.5 cm, wherein the inflated sleeve 260 may be symmetrical about a longitudinal axis 2 of guiding catheter shaft 210, which extends between ends 216P, 216D of sleeve 260, and about its own central and radially extending axis 6. FIG. 4 further illustrates a relatively close spacing S between distal-most opening 214 of guide lumen 201 and distal-facing surface 264 of the inflated sleeve 260, for example, as indicated above, being no more than 0.25 inch (6.4 mm).

The significance of system 500, as described above, will be appreciated in connection with the methods described below in conjunction with FIGS. 5A-D, which are schematics outlining some methods of the present disclosure.

FIG. 5A illustrates an optional introducer sheath 510 having been introduced through a sub-xiphoid access site to provide a passageway for guiding catheter 200, wherein the operator has advanced guiding catheter 200 along epicardial surface 6, within the pericardial sac 15, to position inflatable sleeve 260 in proximity to a target implant site, for example, via the fluoroscopic guidance described above in conjunction with FIG. 1. FIG. 5A further illustrates a navigation tool 570, for example, a mapping catheter or an endoscope, which the operator has advanced through guide lumen 201 to more specifically locate the target implant site, according to some methods. As was mentioned above, shaft 210 of guiding catheter 200 may include a pre-formed curvature (FIG. 2), which may cause catheter 200 to somewhat conform to epicardial surface 6, thereby helping the operator to navigate along surface 6. Once sleeve 260 is positioned, the operator may displace epicardial surface 6 away from the overlying pericardial sac 15 by inflating sleeve 260, for example, via inflation syringe 560 coupled to proximal port 261 of inflation lumen 26, which is formed in handle 250 (FIG. 2).

Figure 5C:
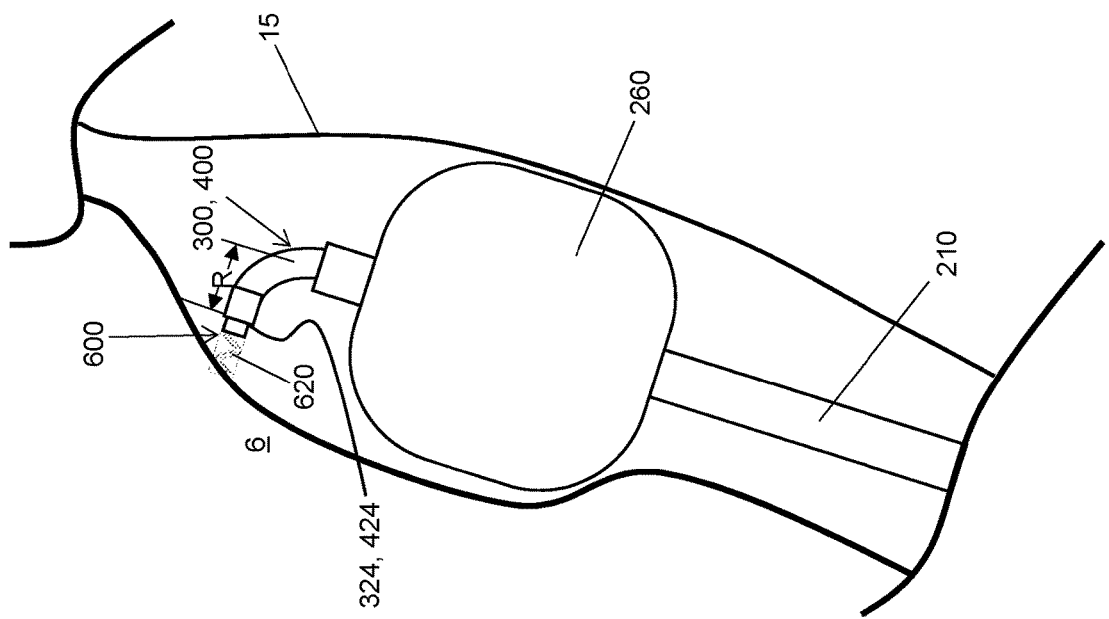
FIG. 5C is an example schematic of the disclosed medical system.
Figure 5B:
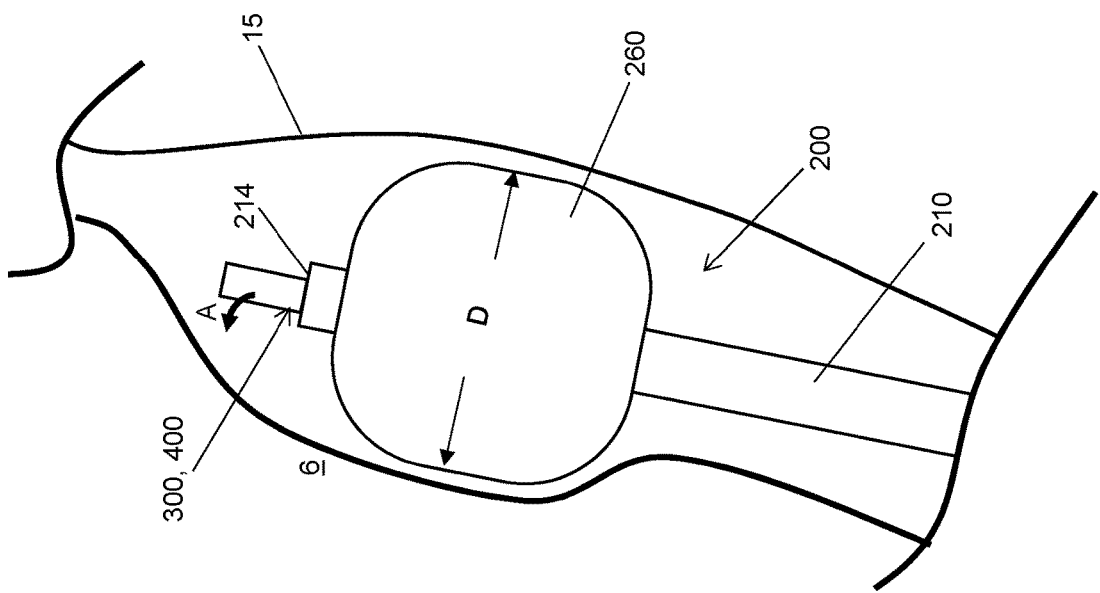
FIG. 5B is an example schematic of the disclosed medical system.

FIG. 5B illustrates sleeve 260 inflated to maximum diameter D so that a resulting gap between the displaced epicardial surface 6 and distal-most opening 214 of guide lumen 201 is at least equal to the above described reach R of delivery catheter 300, 400, for example, as shown in FIG. 5C. With reference back to FIG. 4, the aforementioned relatively close spacing S between distal-most opening 214 and distal-facing surface 264 of inflated sleeve 260 assures that opening 214 remains approximately aligned with longitudinal axis 2. The inflation of sleeve 260 formed from a non-compliant material, according to aforementioned examples, can provide a more controlled and stable displacement of epicardial surface 6 than can a sleeve 260 formed from a compliant material, such as a medical grade Silicone rubber. But, in some instances, a compliant sleeve material may perform adequately in displacing epicardial surface 6.

FIG. 5B further illustrates distal tip segment D3, D4 of delivery catheter 300, 400 extending out from distal-most opening 214 of guide lumen 201, wherein the operator may have advanced delivery catheter 300, 400 to the illustrated position either before or after displacing epicardial surface 6. If delivery catheter 300 is employed, the operator also employs straightening member 30 (FIG. 3A) by initially advancing shaft 31 thereof through delivery lumen 301 to hold adjustable segment A3 in the straight configuration, and then by withdrawing straightening member 30 from delivery lumen 301 to adjust adjustable segment A3 to the curved configuration, per arrow A. Then the operator may advance a medical electrical lead 600 through delivery lumen 301 and out through distal-most opening 324 thereof, for example, as shown in FIG. 5C. Alternately, if delivery catheter 400 is employed, the operator actuates the pull wire mechanism thereof to adjust adjustable segment A4 to the curved configuration, per arrow A, and lead 600 may be advance through delivery lumen 401 either before or after activating reach R of delivery catheter 400.

Once lead 600 is advanced, and a fixation member 620 thereof, for example, a helical member formed from 90/10 Platinum/Iridium, is exposed, as shown in FIG. 5C, the operator may manipulate lead 600 to secure lead 600 to the implant site via fixation member 620. With further reference to FIG. 5C, it may be appreciated how the displacement of epicardial surface 6, via inflatable sleeve 260, allows reach R of delivery catheter 300, 400 to orient lead fixation member 620, relative to epicardial surface 6, in a way that enables the operator to engage a tip thereof with tissue at surface 6, and thereby secure lead 600 to the implant site. After the lead 600 is secured at the implant site, and before deflating sleeve 260 of guiding catheter 200, the operator may withdraw delivery catheter 300, 400 from guide lumen 201 and from around lead 600. After the operator deflates sleeve 260, the operator may remove guiding catheter 200 (and optional introducer sheath 510) from around the secured lead 600.

Figure 5D:
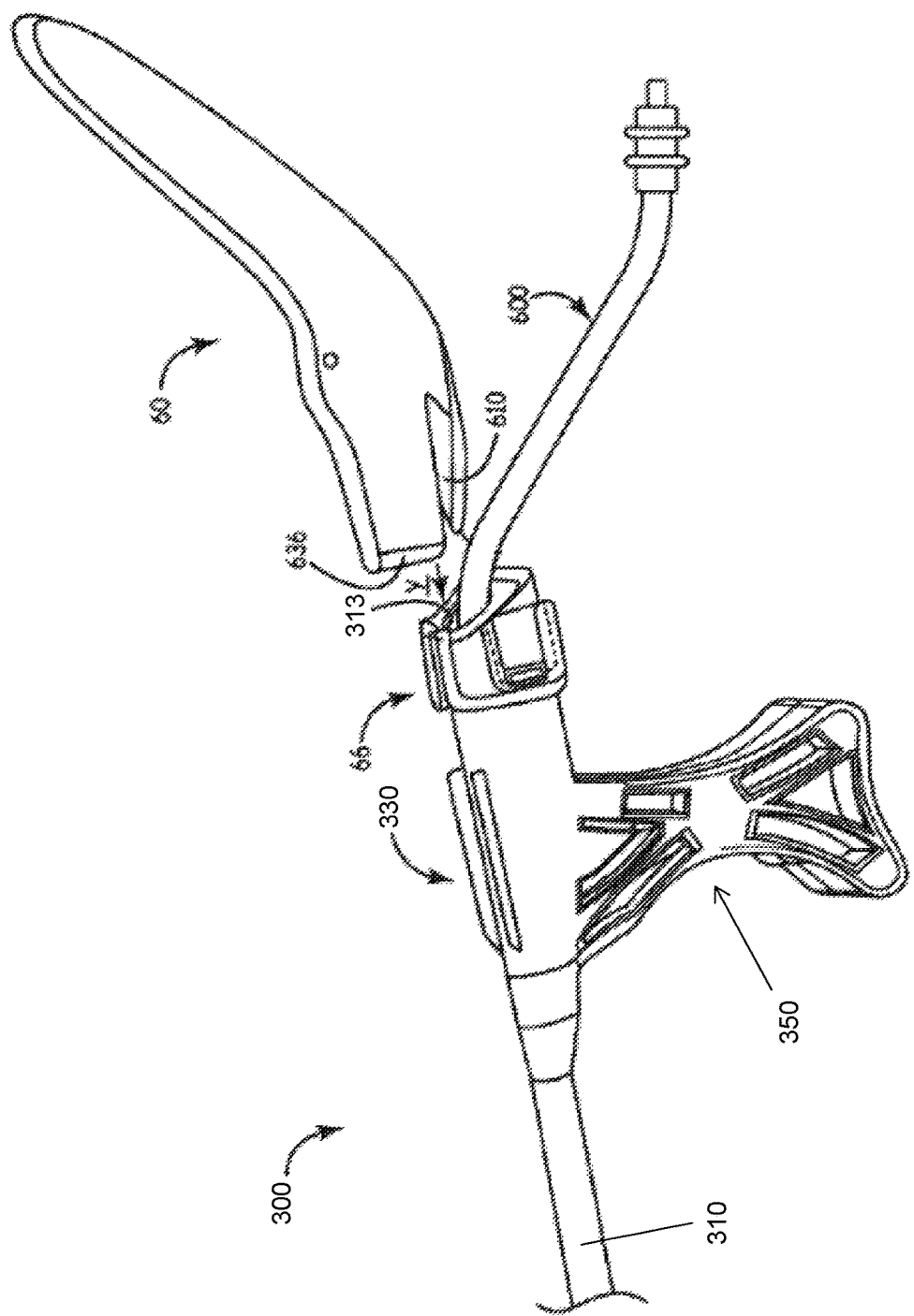
FIG. 5D is an example schematic of the disclosed medical system.

According to some examples and methods, delivery catheter 300 and guiding catheter 200 are configured to be slit for removal from around lead 600, for example, as illustrated in FIG. 5D. Those skilled in the art are familiar with the use of slitting tools to remove catheters from around implanted leads by slitting through the sidewalls of the catheter; and hubs 230, 330 of guiding and delivery catheters may be constructed to facilitate the slitting in a similar manner to that described for a proximal section of a catheter in the aforementioned '872 reference, according to some examples. FIG. 5D shows a slitting tool 60 positioned for insertion, per arrow Y, into proximal opening 313 of delivery catheter 300, alongside lead 600, wherein hub 330 includes an engagement feature 66 for slitting tool 60, which, by engaging a leading edge feature 636 of tool 60, guides a blade 610 of tool 60 into contact with a relatively thin wall section of a relatively rigid sidewall of hub 330 to begin the process of slitting delivery catheter 300 for removal from around lead 600.

Various examples have been described. These and other examples are within the scope of the following claims.

What is claimed is:

1. An interventional medical system configured for implanting an epicardial medical electrical lead, the system comprising:
    a guiding catheter and a delivery catheter; the guiding catheter comprising a shaft that defines a guide lumen, a handle joined to a proximal end of the shaft, and an inflation assembly, the inflation assembly comprising an inflation lumen, which extends within the handle and the shaft, from a proximal port thereof, which is formed in the handle, to a distal port thereof, which is formed in the shaft, in proximity to a distal end thereof, the distal end of the shaft defining a distal-most opening of the guide lumen; and the delivery catheter comprising an elongate tubular member configured for sliding engagement within the guide lumen, the tubular member defining a delivery lumen sized to receive the lead in sliding engagement therewith, the tubular member including a proximal segment, an adjustable segment that extends distally from the proximal segment, and a distal tip segment that extends distally from the adjustable segment, wherein the distal-most edge of the distal tip segment defines a distal-most opening of the delivery lumen,
    wherein the adjustable segment is adjustable from a straight configuration to a curved configuration, wherein the adjustable segment defines a reach in the curved configuration, wherein the reach is a maximum distance from the proximal segment to a distal-most edge of the distal tip segment of the delivery catheter in a direction orthogonal to a longitudinal axis of the delivery catheter,
    wherein the inflation assembly of the guiding catheter comprises a non-compliant inflatable sleeve that, when inflated, has a maximum diameter of at least twice the reach, the sleeve being secured to the shaft of the guiding catheter so that a sealed interior portion thereof is in fluid communication with the inflation lumen via the distal port, and
    wherein the shaft of the guiding catheter defines a spacing between the distal-most opening of the guide lumen and a distal-most facing surface of the inflatable sleeve when the inflatable sleeve is inflated to the maximum diameter, and wherein the spacing is defined to cause the distal-most opening of the guide lumen to remain approximately aligned with a longitudinal axis of the guiding catheter when the inflatable sleeve is inflated to the maximum diameter, such that the maximum diameter is at least twice the reach.

2. The system of claim 1, wherein the reach of the delivery catheter tubular member is between approximately 1 centimeter (cm) and approximately 2 cm.

3. The system of claim 1, wherein an angle through which the distal tip segment of the delivery catheter tubular member moves, between the straight configuration and the curved configuration of the adjustable segment, is no less than 45 degrees and no greater than 90 degrees.

4. The system of claim 1, wherein the non-compliant sleeve of the guiding catheter has an inflated length of between approximately 1.75 centimeters (cm) and approximately 3.5 cm, and wherein an inflated length of the inflatable sleeve is greater than 1.75 centimeters, and wherein the spacing is less than 6.4 millimeters.

5. The system of claim 1, further comprising:
    a straightening member sized for sliding engagement within the lumen of the delivery catheter tubular member; and
    wherein the adjustable segment of the delivery catheter tubular member comprises a flexible sidewall pre-formed to the curved configuration; and
    the straightening member, when engaged within the lumen of the tubular member, holds the adjustable segment in the straight configuration.

6. The system of claim 1, wherein the delivery catheter further comprises a pull wire mechanism configured to adjust the adjustable segment of the tubular member of the delivery catheter between the straight and curved configurations.

7. The system of claim 1, wherein the tubular member includes a flexible sidewall pre-formed to the curved configuration to activate the reach when the adjustable segment extends distally from the proximal segment of the tubular member.

8. The system of claim 1, wherein the inflatable sleeve has a proximal end and a distal end, wherein the proximal end is secured to the shaft of the guiding catheter and the distal end is secured to the shaft of the guiding catheter.

9. The system of claim 1, wherein the sealed interior portion is bounded by an interior portion of the non-compliant inflatable sleeve and an exterior surface of the shaft of the guiding catheter.

10. The system of claim 1 further comprising a hub, wherein the handle is joined to the hub.

11. The system of claim 10, wherein the hub defines a proximal opening into the guide lumen.

12. The system of claim 1,
    wherein the inflatable sleeve is configured to displace a tissue surface to define a gap between the displaced tissue surface and the distal-most opening of the guide lumen when the inflatable sleeve is inflated to the maximum diameter, and
    wherein the gap is at least equal to the reach defined by the adjustable segment of the tubular member, and
    wherein the tubular member is configured to orient a fixation member of the lead to engage the fixation member with the tissue surface when the adjustable segment defines the reach, the inflatable sleeve defines the gap, and the tubular member receives the lead in the delivery lumen.

13. A medical system comprising:
    a guiding catheter, the guiding catheter comprising:
    a shaft defining a guide lumen, wherein a distal end of the shaft defines a distal-most opening of the guide lumen;
    a handle joined to a proximal end of the shaft;

a hub joined to the handle, wherein the hub defines a proximal opening into the guide lumen; and
an inflation lumen extending within the handle and the shaft, the inflation lumen comprising:
a proximal port formed in the handle; and
a distal port formed in the shaft in proximity to the distal end of the shaft;
an inflatable sleeve having a proximal end and a distal end,
wherein the proximal end is secured to the shaft of the guiding catheter and the distal end is secured to the shaft of the guiding catheter,
wherein a sealed interior portion of the inflatable sleeve between the proximal end of the inflatable sleeve and the distal end of the inflatable sleeve is bounded by the inflatable sleeve and the shaft of the guiding catheter,
wherein the sealed interior portion is in fluid communication with the distal port of the inflation lumen, and
wherein the inflatable sleeve is configured to inflate to a maximum diameter; and
a delivery catheter comprising an elongate tubular member defining a delivery lumen and configured for sliding engagement within the guide lumen,
wherein the elongate tubular member comprises a proximal segment, an adjustable segment extending distally from the proximal segment, and a distal tip segment extending distally from the adjustable segment,
wherein the distal tip segment defines a distal most edge,
wherein the adjustable segment is adjustable between a straight configuration and a pre-formed curved configuration,
wherein when the adjustable segment is in the pre-formed curved configuration and the adjustable segment extends distally from the proximal segment of the tubular member, a reach is defined by a maximum distance from the proximal segment to the distal-most edge of the distal tip segment in a direction orthogonal to a longitudinal axis of the delivery catheter, and
wherein the shaft of the guiding catheter defines a spacing between the distal-most opening of the guide lumen and a distal-most facing surface of the inflatable sleeve when the inflatable sleeve is inflated to the maximum diameter, and wherein the spacing is defined to cause the distal-most opening of the guide lumen to remain aligned with the longitudinal axis of the guiding catheter when the inflatable sleeve is inflated to the maximum diameter, such that the maximum diameter of the inflatable segment is at least twice the reach.

14. The system of claim 13, wherein the inflatable sleeve, when inflated, has an inflated length of between approximately 1.75 centimeters (cm) and approximately 3.5 cm.

15. The medical system of claim 13, wherein the spacing is less than 0.25 inch (6.4 millimeters (mm)).

16. The system of claim 13, wherein the reach is between approximately 1 centimeter (cm) and approximately 2 cm.

17. The system of claim 13, wherein an angle through which the distal tip segment of the delivery catheter moves, between the straight configuration and the curved configuration of the adjustable segment, is no less than 45 degrees and no greater than 90 degrees.

18. The system of claim 13, further comprising a straightening member sized for sliding engagement within the delivery lumen of the elongate tubular member,
wherein the adjustable segment of the elongate tubular member comprises a flexible sidewall pre-formed to the curved configuration, and
wherein the straightening member, when engaged within the delivery lumen of the elongate tubular member, holds the adjustable segment in the straight configuration.

19. The system of claim 13, wherein the delivery catheter further comprises a pull wire mechanism configured to adjust the adjustable segment of the elongate tubular member between the straight and curved configurations.

20. The system of claim 13, wherein the shaft of the guiding catheter includes a pre-formed curvature in proximity to, and proximal to the inflatable sleeve, no radius of the pre-formed curvature being less than approximately 5 centimeters (cm).

* * * * *